United States Patent
Cruise et al.

(10) Patent No.: US 11,998,563 B2
(45) Date of Patent: *Jun. 4, 2024

(54) POLYMERIC TREATMENT COMPOSITIONS

(71) Applicant: MicroVention, Inc., Aliso Viejo, CA (US)

(72) Inventors: Gregory M. Cruise, Rancho Santa Margarita, CA (US); Michael J. Constant, Mission Viejo, CA (US); Joshua Garretson, San Diego, CA (US)

(73) Assignee: MicroVention, Inc., Aliso Viejo, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/744,192

(22) Filed: May 13, 2022

(65) Prior Publication Data
US 2022/0273700 A1    Sep. 1, 2022

Related U.S. Application Data

(60) Continuation of application No. 16/806,936, filed on Mar. 2, 2020, now Pat. No. 11,331,340, which is a
(Continued)

(51) Int. Cl.
*A61K 31/785* (2006.01)
*A61K 9/00* (2006.01)
(Continued)

(52) U.S. Cl.
CPC .......... *A61K 31/785* (2013.01); *A61K 9/0024* (2013.01); *A61K 31/78* (2013.01);
(Continued)

(58) Field of Classification Search
CPC .... A61K 31/785; A61K 9/0024; A61K 31/78; A61K 47/32; A61L 24/0089; A61L 24/046; A61L 2430/36
See application file for complete search history.

(56) References Cited

U.S. PATENT DOCUMENTS

| | | | |
|---|---|---|---|
| 3,852,341 | A | 12/1974 | Bjork et al. |
| 4,406,878 | A | 9/1983 | Boer et al. |

(Continued)

FOREIGN PATENT DOCUMENTS

| | | |
|---|---|---|
| CA | 2551373 C | 6/2014 |
| CN | 101513542 B | 8/2012 |

(Continued)

OTHER PUBLICATIONS

Argawal et al., Chitosan-based systems for molecular imaging. Advanced Drug Delivery Reviews, 62:42-48 (2010).
(Continued)

*Primary Examiner* — Jianfeng Song
(74) *Attorney, Agent, or Firm* — K&L Gates LLP; Brian J. Novak; Giorgios N. Kefallinos

(57) ABSTRACT

Compositions are described comprising a polymer; a non-physiological pH solution; and a visualization agent; wherein the polymer is soluble in the non-physiological pH solution and insoluble at a physiological pH. Methods of forming the solutions and polymers are disclosed as well as methods of therapeutic use.

11 Claims, 4 Drawing Sheets

Related U.S. Application Data continuation of application No. 16/232,929, filed on Dec. 26, 2018, now Pat. No. 10,588,923, which is a continuation of application No. 15/924,028, filed on Mar. 16, 2018, now Pat. No. 10,201,562, which is a continuation of application No. 15/142,395, filed on Apr. 29, 2016, now Pat. No. 9,937,201, which is a division of application No. 13/917,323, filed on Jun. 13, 2013, now Pat. No. 9,351,993.

(60) Provisional application No. 61/659,916, filed on Jun. 14, 2012.

(51) Int. Cl.
*A61K 31/78* (2006.01)
*A61L 24/00* (2006.01)
*A61L 24/04* (2006.01)
*A61K 47/32* (2006.01)

(52) U.S. Cl.
CPC ......... *A61L 24/0089* (2013.01); *A61L 24/046* (2013.01); *A61K 47/32* (2013.01); *A61L 2430/36* (2013.01)

(56) References Cited

U.S. PATENT DOCUMENTS

| | | |
|---|---|---|
| 5,580,568 A | 12/1996 | Greff et al. |
| 5,667,767 A | 9/1997 | Greff et al. |
| 5,695,480 A | 12/1997 | Evans et al. |
| 5,702,361 A | 12/1997 | Evans et al. |
| 5,755,658 A | 5/1998 | Wallace et al. |
| 5,823,198 A | 10/1998 | Jones et al. |
| 5,830,178 A | 11/1998 | Jones et al. |
| 5,851,508 A | 12/1998 | Greff et al. |
| 5,894,022 A | 4/1999 | Ji et al. |
| 6,004,573 A | 12/1999 | Rathi et al. |
| 6,015,541 A | 1/2000 | Greff et al. |
| 6,017,977 A | 1/2000 | Evans et al. |
| 6,037,366 A | 3/2000 | Krall et al. |
| 6,040,408 A | 3/2000 | Koole |
| 6,051,607 A | 4/2000 | Greff et al. |
| 6,146,373 A | 11/2000 | Cragg et al. |
| 6,281,263 B1 | 8/2001 | Evans et al. |
| 6,303,100 B1 | 10/2001 | Ricci et al. |
| 6,333,020 B1 | 12/2001 | Wallace et al. |
| 6,335,384 B1 | 1/2002 | Evans et al. |
| 6,342,202 B1 | 1/2002 | Evans et al. |
| 6,394,945 B1 | 5/2002 | Chan et al. |
| 6,454,738 B1 | 9/2002 | Tran et al. |
| 6,475,477 B1 | 11/2002 | Kohn et al. |
| 6,503,244 B2 | 1/2003 | Hayman |
| 6,511,468 B1 | 1/2003 | Cragg et al. |
| 6,511,472 B1 | 1/2003 | Hayman et al. |
| 6,531,111 B1 | 3/2003 | Whalen et al. |
| 6,558,367 B1 | 5/2003 | Cragg et al. |
| 6,562,362 B1 | 5/2003 | Bae et al. |
| 6,565,551 B1 | 5/2003 | Jones et al. |
| 6,569,190 B2 | 5/2003 | Whalen et al. |
| 6,599,448 B1 | 7/2003 | Ehrhard et al. |
| 6,602,269 B2 | 8/2003 | Wallace et al. |
| 6,610,046 B1 | 8/2003 | Usami et al. |
| 6,616,591 B1 | 9/2003 | Teoh et al. |
| 6,623,450 B1 | 9/2003 | Dutta et al. |
| 6,645,167 B1 | 11/2003 | Whalen, II et al. |
| 6,699,222 B1 | 3/2004 | Jones et al. |
| 6,756,031 B2 | 6/2004 | Evans et al. |
| 6,759,028 B2 | 7/2004 | Wallace et al. |
| 6,962,689 B2 | 11/2005 | Whalen et al. |
| 6,964,657 B2 | 11/2005 | Cragg et al. |
| 6,979,464 B2 | 12/2005 | Gutowska |
| 7,018,365 B2 | 3/2006 | Strauss et al. |
| 7,070,607 B2 | 7/2006 | Murayama et al. |
| 7,083,643 B2 | 8/2006 | Whalen et al. |
| 7,138,106 B2 | 11/2006 | Evans et al. |
| 7,374,568 B2 | 5/2008 | Whalen et al. |
| 7,459,142 B2 | 12/2008 | Greff |
| 7,476,648 B1 | 1/2009 | Tabata et al. |
| 7,507,229 B2 | 3/2009 | Hewitt et al. |
| 7,507,394 B2 | 3/2009 | Whalen et al. |
| 7,776,063 B2 | 8/2010 | Sawhney et al. |
| 7,790,141 B2 | 9/2010 | Pathak et al. |
| 7,838,699 B2 | 11/2010 | Schwarz et al. |
| 7,976,527 B2 | 7/2011 | Cragg et al. |
| 8,066,667 B2 | 11/2011 | Hayman et al. |
| 8,235,941 B2 | 8/2012 | Hayman et al. |
| 8,454,649 B2 | 6/2013 | Cragg et al. |
| 8,486,046 B2 | 7/2013 | Hayman et al. |
| 8,492,329 B2 | 7/2013 | Shemesh et al. |
| 8,685,367 B2 | 4/2014 | Brandom et al. |
| 9,078,950 B2 | 7/2015 | Cruise et al. |
| 9,351,993 B2 | 5/2016 | Cruise et al. |
| 9,434,800 B2 | 9/2016 | Chevalier et al. |
| 9,655,989 B2 | 5/2017 | Cruise et al. |
| 9,907,880 B2 | 3/2018 | Cruise et al. |
| 9,937,201 B2 | 4/2018 | Cruise et al. |
| 10,201,562 B2 | 2/2019 | Cruise et al. |
| 10,258,716 B2 | 4/2019 | Cruise et al. |
| 10,368,874 B2 | 8/2019 | Baldwin et al. |
| 10,576,182 B2 | 3/2020 | Cruise et al. |
| 10,588,923 B2 | 3/2020 | Cruise et al. |
| 10,828,388 B2 | 11/2020 | Cruise et al. |
| 11,051,826 B2 | 7/2021 | Baldwin et al. |
| 11,331,340 B2 | 5/2022 | Cruise et al. |
| 2001/0022962 A1 | 9/2001 | Greff et al. |
| 2001/0024637 A1 | 9/2001 | Evans et al. |
| 2001/0033832 A1 | 10/2001 | Wallace et al. |
| 2001/0036451 A1 | 11/2001 | Goupil et al. |
| 2001/0046518 A1 | 11/2001 | Sawhney |
| 2002/0026234 A1 | 2/2002 | Li et al. |
| 2002/0042378 A1 | 4/2002 | Reich et al. |
| 2003/0021762 A1 | 1/2003 | Luthra et al. |
| 2003/0040733 A1 | 2/2003 | Cragg et al. |
| 2003/0099597 A1* | 5/2003 | Whalen, II ............. A61L 24/02 424/78.37 |
| 2003/0100942 A1 | 5/2003 | Ken et al. |
| 2003/0147825 A1* | 8/2003 | Chiarelli ............. A61K 8/8158 424/70.11 |
| 2003/0211083 A1 | 11/2003 | Vogel et al. |
| 2003/0232198 A1 | 12/2003 | Lamberti et al. |
| 2004/0024098 A1 | 2/2004 | Mather et al. |
| 2004/0091425 A1 | 5/2004 | Boschetti |
| 2004/0091543 A1 | 5/2004 | Bell et al. |
| 2004/0157082 A1 | 8/2004 | Ritter et al. |
| 2004/0158282 A1 | 8/2004 | Jones et al. |
| 2004/0161547 A1 | 8/2004 | Carlson et al. |
| 2004/0209998 A1 | 10/2004 | De Vries |
| 2004/0224864 A1 | 11/2004 | Patterson et al. |
| 2004/0228797 A1 | 11/2004 | Bein et al. |
| 2004/0241158 A1 | 12/2004 | McBride et al. |
| 2005/0003010 A1 | 1/2005 | Cohen et al. |
| 2005/0008610 A1 | 1/2005 | Schwarz et al. |
| 2005/0106119 A1 | 5/2005 | Brandom et al. |
| 2005/0123596 A1* | 6/2005 | Kohane ............. A61K 9/5153 435/458 |
| 2005/0143484 A1 | 6/2005 | Fang et al. |
| 2005/0175709 A1 | 8/2005 | Baty et al. |
| 2005/0196449 A1 | 9/2005 | DiCarlo et al. |
| 2005/0226935 A1 | 10/2005 | Kamath et al. |
| 2005/0244504 A1 | 11/2005 | Little et al. |
| 2005/0265923 A1 | 12/2005 | Toner et al. |
| 2006/0008499 A1 | 1/2006 | Hudak |
| 2006/0067883 A1 | 3/2006 | Krom et al. |
| 2006/0069168 A1 | 3/2006 | Tabata et al. |
| 2006/0088476 A1 | 4/2006 | Harder et al. |
| 2006/0134054 A1* | 6/2006 | Kulkarni ............. C08F 220/14 424/70.16 |
| 2006/0233854 A1 | 10/2006 | Seliktar et al. |
| 2007/0026039 A1 | 2/2007 | Drumheller et al. |
| 2007/0196454 A1 | 8/2007 | Stockman et al. |
| 2007/0208141 A1 | 9/2007 | Shull et al. |
| 2007/0224234 A1 | 9/2007 | Steckel et al. |
| 2007/0231366 A1 | 10/2007 | Sawhney et al. |

(56) References Cited

U.S. PATENT DOCUMENTS

| | | |
|---|---|---|
| 2007/0237741 A1 | 10/2007 | Figuly et al. |
| 2007/0248567 A1 | 10/2007 | Pathak et al. |
| 2008/0019921 A1 | 1/2008 | Zhang |
| 2008/0038354 A1 | 2/2008 | Slager et al. |
| 2008/0039890 A1 | 2/2008 | Matson et al. |
| 2008/0114277 A1 | 5/2008 | Ambrosio et al. |
| 2008/0214695 A1 | 9/2008 | Pathak et al. |
| 2008/0226741 A1 | 9/2008 | Richard |
| 2008/0243129 A1 | 10/2008 | Steffen et al. |
| 2008/0269874 A1 | 10/2008 | Wang et al. |
| 2008/0281352 A1 | 11/2008 | Ingenito et al. |
| 2009/0041850 A1 | 2/2009 | Figuly |
| 2009/0048659 A1 | 2/2009 | Weber et al. |
| 2009/0054535 A1 | 2/2009 | Figuly et al. |
| 2009/0093550 A1 | 4/2009 | Rolfes et al. |
| 2009/0117033 A1 | 5/2009 | O'Gara |
| 2009/0117070 A1 | 5/2009 | Daniloff et al. |
| 2009/0181068 A1 | 7/2009 | Dunn |
| 2009/0186061 A1 | 7/2009 | Griguol et al. |
| 2009/0215923 A1 | 8/2009 | Carnahan et al. |
| 2009/0221731 A1 | 9/2009 | Vetrecin et al. |
| 2009/0259302 A1 | 10/2009 | Trollsas et al. |
| 2009/0297612 A1 | 12/2009 | Koole et al. |
| 2010/0010159 A1 | 1/2010 | Belcheva |
| 2010/0023112 A1 | 1/2010 | Borck et al. |
| 2010/0036491 A1 | 2/2010 | He et al. |
| 2010/0042067 A1 | 2/2010 | Koehler |
| 2010/0049165 A1 | 2/2010 | Sutherland et al. |
| 2010/0080788 A1 | 4/2010 | Barnett et al. |
| 2010/0086678 A1 | 4/2010 | Arthur et al. |
| 2010/0158802 A1 | 6/2010 | Hansen et al. |
| 2010/0247663 A1 | 9/2010 | Day et al. |
| 2010/0256777 A1 | 10/2010 | Datta et al. |
| 2010/0303804 A1 | 12/2010 | Liska et al. |
| 2011/0008406 A1 | 1/2011 | Altman et al. |
| 2011/0008442 A1 | 1/2011 | Zawko et al. |
| 2011/0020236 A1 | 1/2011 | Bohmer et al. |
| 2011/0071495 A1 | 3/2011 | Tekulve |
| 2011/0091549 A1 | 4/2011 | Blaskovich et al. |
| 2011/0105889 A1 | 5/2011 | Tsukada et al. |
| 2011/0182998 A1 | 7/2011 | Reb et al. |
| 2011/0190813 A1 | 8/2011 | Brownlee et al. |
| 2011/0202016 A1 | 8/2011 | Zugates et al. |
| 2011/0207232 A1 | 8/2011 | Ostafin et al. |
| 2012/0041481 A1 | 2/2012 | Daniloff et al. |
| 2012/0059394 A1 | 3/2012 | Brenner et al. |
| 2012/0114589 A1 | 5/2012 | Rolfes-Meyering et al. |
| 2012/0156164 A1 | 6/2012 | Park et al. |
| 2012/0164100 A1 | 6/2012 | Li et al. |
| 2012/0184642 A1 | 7/2012 | Bartling et al. |
| 2012/0238644 A1 | 9/2012 | Gong et al. |
| 2012/0244198 A1 | 9/2012 | Malmsjo et al. |
| 2013/0039848 A1 | 2/2013 | Bradbury et al. |
| 2013/0045182 A1 | 2/2013 | Gong et al. |
| 2013/0060230 A1 | 3/2013 | Capistron et al. |
| 2013/0079421 A1 | 3/2013 | Aviv et al. |
| 2013/0108574 A1 | 5/2013 | Chevalier et al. |
| 2013/0184660 A1 | 7/2013 | Swiss et al. |
| 2013/0225778 A1 | 8/2013 | Goodrich et al. |
| 2014/0039459 A1 | 2/2014 | Folk et al. |
| 2014/0056806 A1 | 2/2014 | Vernengo et al. |
| 2014/0171907 A1 | 6/2014 | Golzarian et al. |
| 2014/0274945 A1 | 9/2014 | Blaskovich et al. |
| 2014/0277057 A1 | 9/2014 | Ortega et al. |
| 2015/0290344 A1 | 10/2015 | Alexis et al. |
| 2017/0274101 A1 | 9/2017 | Hainfeld |
| 2020/0246501 A1 | 8/2020 | Cruise et al. |
| 2021/0023261 A1 | 1/2021 | Cruise et al. |
| 2021/0290816 A1 | 9/2021 | Fitz et al. |
| 2021/0330334 A1 | 10/2021 | Baldwin et al. |

FOREIGN PATENT DOCUMENTS

| | | |
|---|---|---|
| CN | 102107025 B | 5/2014 |
| EP | 1599258 B1 | 8/2008 |
| EP | 1601392 B1 | 4/2009 |
| EP | 1558299 B1 | 12/2012 |
| JP | 05-057014 | 3/1993 |
| JP | 1993253283 A | 10/1993 |
| JP | 11-166018 | 6/1999 |
| WO | 1996/005872 | 2/1996 |
| WO | 2004/073843 A1 | 9/2004 |
| WO | 2004/074434 A2 | 9/2004 |
| WO | 2005/013810 A2 | 2/2005 |
| WO | 2005/030268 A1 | 4/2005 |
| WO | 2006/095745 A1 | 9/2006 |
| WO | 2008/118662 A2 | 10/2008 |
| WO | 2011/110589 A1 | 9/2011 |
| WO | 2012/019145 A1 | 2/2012 |
| WO | 2012/025023 A1 | 3/2012 |
| WO | 2012/088896 A1 | 7/2012 |
| WO | 2012/171478 A1 | 12/2012 |
| WO | 2013/188681 A1 | 12/2013 |
| WO | 2014/062696 A1 | 4/2014 |
| WO | 2014/152488 A2 | 9/2014 |
| WO | 2019/074965 A1 | 4/2019 |

OTHER PUBLICATIONS

Dudeck O, Jordan O, Hoffmann KT, et al. Embolization of experimental wide-necked aneurysms with iodine-containing polyvinyl alcohol solubilized in a low-angiotoxicity solvent. AJNR Am J Neuroradiol. 2006;27(9):1849-1855.

Dudeck O, Jordan O, Hoffmann KT, et al. Organic solvents as vehicles for precipitating liquid embolics: a comparative angiotoxicity study with superselective injections of swine rete mirabile. AJNR Am J Neuroradiol. 2006;27(9):1900-1906.

He et al., Material properties and cytocompatibility of injectable MMP degradable poly(lactide ethylene oxide fumarate) hydrogel as a carrier for marrow stromal cells. Biomacromolecules, vol. 8, pp. 780-792 (2007).

Levasque et al., Synthesis of enzyme-degradable, peptide-cross-linked dextran hydrogels. Bionconjugate Chemistry, vol. 18, pp. 874-885 (2007).

Moss et al., Solid-Phase synthesis and kinetic characterization of fluorogenic enzyme-degradable hydrogel cross-linkers. Biomacromolecules, vol. 7, pp. 1011-1016 (2006).

Onyx Liquid Embolic System Onyx HD-500, Instructions for Use, ev3 Endovascular, Inc., Nov. 2007.

Supplementary European Search Report dated Sep. 26, 2016 for European Patent Application No. 13846860.8 filed on Oct. 15, 2013.

Takao H, Murayama Y, Yuki I, et al. Endovascular treatment of experimental aneurysms using a combination of thermoreversible gelation polymer and protection devices: feasibility study. Neurosurgery. 2009;65(3):601-609.

Jayakrishnan et al., Synthesis and polymerization of some iodine-containing monomers for biomedical applications. Journal of Applied Polymer Science, vol. 44, pp. 743-748 (1992).

International Search Report and Written Opinion, dated Dec. 31, 2018, for International Application No. PCT/US2018/055074.

International Search Report and Written Opinion, dated Jan. 2, 2014, for International Application No. PCT/US2013/065078.

Wikipedia, "Isotopes of Iodine" Version: Jun. 15, 2017, Retrieved: Nov. 26, 2018 (https://en.wikipedia.org/w/index.php?title=isotopes_of_iodine&oldid=785724472), p. 2, para 7.

Arslan et al., Use of 4-vinylpyridine and 2-hydroxyethylmethacrylate monomer mixture grafted poly(ethylene terephthalate) fibers for removal of congo red from aqueous solution. E-Polymers, vol. 8, Issue 1, 016, pp. 1-15 (2008).

Shin et al., Inverse opal pH sensors with various protic monomers copolymerized with polyhydroxyethylmethacrylate hyrdrogel. Analytica Chimica Acta, 752:87-93 (2012).

Yi et al., Ionic strength/temperature-induced gelation of aqueous poly(N-isopropylacrylamide-co-vinylimidazole) solution. Macromol. Symp. 207, pp. 131-137 (2004).

Kocer et al., Preliminary experience with precipitating hydrophobic injectable liquid in brain arteriovenous malformations. Diagn Interv Radiol, 22:184-189 (2016).

(56) References Cited

OTHER PUBLICATIONS

International Search Report for International Application No. PCT/US2013/045692 filed on Jun. 13, 2013.
Extended European Search Report, dated Mar. 22, 2022, for European Application Serial No. 21206809.2.
Du et al., Dextran gadolinium complex containing folate groups as a potential magnetic resonance imaging contrast agent. Chinese Journal of Polymer Sience, 33(9):1325-1333 (2015).

* cited by examiner

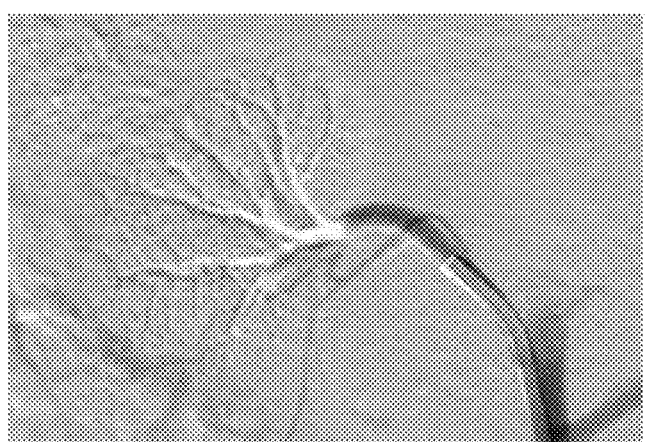
FIG. 5A
FIG. 5B

POLYMERIC TREATMENT COMPOSITIONS

CROSS REFERENCE TO RELATED APPLICATIONS

This application is a continuation of U.S. patent application Ser. No. 16/806,936 filed Mar. 2, 2020, which is a continuation of U.S. patent application Ser. No. 16/232,929 filed Dec. 26, 2018, now U.S. Pat. No. 10,588,923, which is a continuation of U.S. patent application Ser. No. 15/924,028 filed Mar. 16, 2018, now U.S. Pat. No. 10,201,562, which is a continuation of U.S. patent application Ser. No. 15/142,395 filed Apr. 29, 2016, now U.S. Pat. No. 9,937,201, which is a divisional of U.S. patent application Ser. No. 13/917,323 filed Jun. 13, 2013, now U.S. Pat. No. 9,351,993, which claims the benefit of U.S. provisional patent application No. 61/659,916, filed Jun. 14, 2012, the entire disclosures of which are incorporated herein by reference.

FIELD

The present invention relates generally to vascular treatment compositions and methods of using these compositions to treat vascular conditions. The compositions can comprise a polymer(s) that transition from a liquid to a solid upon being subject to a physiological pH generally found in a tissue or lumen.

BACKGROUND

Embolization is widely used to treat vascular malformations, such as aneurysms, arteriovenous malformations, fistulas, and tumors. These malformations can be treated with a variety of different products, including metallic coils, polymer-metal hybrid coils, microparticles, glues, and foams. However, there remains a need for products that can minimize the risks associated with embolization.

SUMMARY

Treatment compositions are described which comprise a polymer; a solution, e.g., an aqueous solution, having a non-physiological pH; and a visualization agent; wherein the polymer is soluble in the non-physiological pH solution and insoluble in a physiological pH. In some embodiments, the polymer is biocompatible.

Methods of delivering a composition as described herein are also described comprising injecting through a delivery device to a location with a physiological pH a liquid embolic composition comprising a polymer, a solution having a non-physiological pH and a visualization agent, wherein the polymer precipitates when it reaches the physiological pH and treats the vascular disorder.

Methods of treating a vascular disorder are also described comprising injecting through a delivery device into a vessel with a physiological pH environment a liquid embolic composition comprising a polymer, a solution having a non-physiological pH and a visualization agent, wherein the polymer precipitates when it reaches the physiological pH and treats the vascular disorder.

The visualization agent can be a particulate and can have a concentration of about % w/w to about 65% w/w. Depending on the type of imaging used with the present compositions, the visualization agent can be iodinated compounds, metal particles, barium sulfate, superparamagnetic iron oxide, gadolinium molecules or a combination thereof.

The polymer can be a reaction product of two or more different monomers or a reaction product of three different monomers. In other embodiments, the polymer can be a reaction product of one or more different monomers. The polymer can have a concentration between about 1% w/w and about 35% w/w. Again, in some embodiments, the polymer can be biocompatible.

The solution having a non-physiological pH can be aqueous and can have a pH of less than about 7. In other embodiments, the solution has a pH of greater than about 8.

In one embodiment, a composition is described for treating vascular defects comprised of a biocompatible polymer at a concentration of from about 1% to 35% w/w soluble in a solution having a non-physiological pH and insoluble in a physiological pH aqueous solution; a solution having a non-physiological pH; and a particulate visualization agent at a concentration of from about 20% w/w to about 60% w/w.

In another embodiment, methods of treating a vascular disorder are described comprising providing a liquid embolic composition comprising a polymer, a solution having a non-physiological pH and a visualization agent, wherein the polymer is soluble in the solution having a non-physiological pH and insoluble in a physiological pH environment; inserting a delivery device into a vessel or tissue; guiding the delivery device to an area in need of treatment wherein the area has a physiological pH; injecting the liquid embolic polymer composition through the delivery device into the vessel at the area in need of treatment thereby immediately precipitating the polymer and forming a solid polymeric mass; and treating the vascular condition.

BRIEF DESCRIPTION OF THE DRAWINGS

FIGS. 5A and 5B illustrate a post treatment angiogram and a post-treatment CT angiogram of renal vasculature in a rabbit according to Example 7 for visualization comparison.

DETAILED DESCRIPTION

Figure 1:
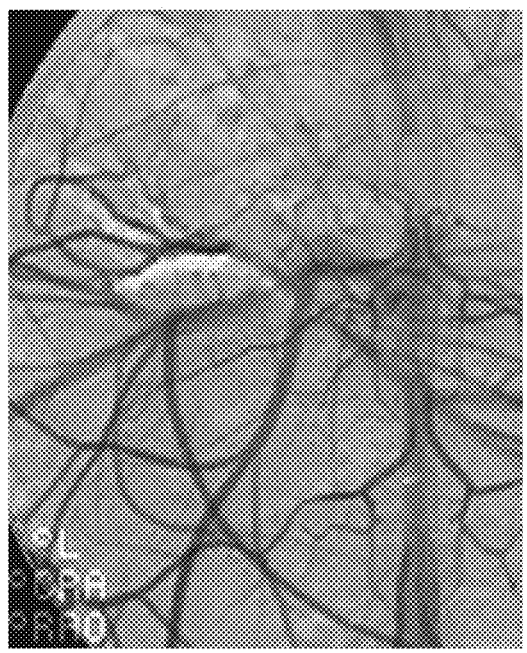
FIG. 1 illustrates a one month follow-up angiogram of a kidney treated with a polymer administered according to Example 5.

Described herein generally are vascular treatment compositions comprising (i) a polymer that can be soluble in solutions at non-physiological pH and insoluble at a physiological pH or when subjected to a physiological pH, (ii) an aqueous solution with a non-physiological pH, and (iii) an opacification agent(s) that can permit visualization in vivo. These compositions can be introduced through a delivery device in the liquid state and transition to the solid state once in the body at subjected to a physiological pH. In one embodiment, the aqueous solution does not include an organic solvent.

When the polymer is soluble, it can be deployed through a delivery device. A delivery device can be any device suitable to deliver the liquid embolic polymers described herein. For example, a delivery device can be a catheter or a microcatheter that is deployed to a delivery site and/or treatment site. However, once precipitated out of solution, the polymer can be much more difficult to deploy. For example, once precipitated, the polymer can in some instances reduce the ability to deliver the polymer through a delivery device. As such, the compositions and methods described herein can provide a polymer treatment solution the can be deployed to a treatment site and having it precipitate once at the location of interest; the precipitated product would generally not be deliverable.

Treatment site and/or delivery site as used herein can be any site within a living creature. In some embodiments, the creature is a mammal such as a human. Human sites can include blood vessels, renal lumens, fatty tissue, muscle, connective tissue, cerebral spinal fluid, brain tissue, repertory tissue, nerve tissue, subcutaneous tissue, intra atria tissue, gastrointestinal tissue, and the like. As a skilled artisan understands, the physiological pH of different tissues and lumens within a mammalian body such as a human can vary. A polymeric solution can be customized for a particular delivery site pH. For example, if the polymer solution is to be delivered to the stomach, where pHs tend to be acidic, the polymeric solution can be formed in as an alkaline solution.

A function of the polymer, e.g. liquid embolic polymer, can be to precipitate when coming in contact with blood or other physiological fluid at a physiological pH at the intended site of treatment. In some embodiments, physiological pH of the blood stream can be a pH of about 7.0, about 7.1, about 7.2, about 7.3, about 7.4, about 7.5, about 7.6, about 7.7 or about 7.8. In another embodiment, physiological pH of the stomach can be a pH of about 3.5, about 3.6, about 3.7, about 3.8, about 3.9, about 4.0, about 4.1, about 4.2, about 4.3, about 4.4, or about 4.5. In still another embodiment, physiological pH of the intestines can depend on the location within the intestines, but generally can be a pH of about 5.5, about 5.6, about 5.7, about 5.8, about 5.9, about 6.0, about 6.1, about 6.2, about 6.3, about 6.4, about 6.5, about 6.6, about 6.7, about 6.8, about 6.9, or about 7.0. Ranges of pH for any of the lists above can be created between any set of values listed. Precipitation of the polymer at a physiological pH can be used to occlude a biological structure and/or a tissue. Control of the liquid embolic polymer's solubility can be achieved by selection of the composition of the polymer.

The vascular treatment compositions can comprise a solution at a non-physiological pH. The solution may be aqueous. The solution can include a polymer soluble in the solution at non-physiological pH but insoluble in a physiological pH. Further included in the solution can be a visualization agent. This change in solubility can be a result in a changing viscosity of the polymer within the solution. In other embodiments, this change in solubility can result in a change in density of the polymer in solution.

The polymer can be prepared with monomers having ionizable moieties. In some embodiments, the polymers can be a reaction product of two different monomers, three different monomers, four different monomers, five different monomers or more. A hydrophobic polymer can be constructed with a minimum amount of ionizable moieties to render the polymer soluble in non-physiological pH solutions. The ratio of monomers with ionizable moieties and other monomers can be dependent on the structure of the monomers and can be determined experimentally.

Amine-containing liquid embolic polymers can be dissolved in a low pH solution, the amines may be substantially protonated and can enhance the solubility of the polymer. The resulting solution can be placed in conditions with a physiological pH and the amines can deprotonate and render the polymer insoluble. Conversely, carboxylic acid-containing polymers can be dissolved in a high pH solution, the carboxylic acids can be substantially deprotonated and enhance the solubility of the polymer. The resulting solution can be placed in conditions with a physiological pH and the carboxylic acids can protonate and render the polymer insoluble.

Monomers with ionizable moieties can contain a polymerizable moiety and can contain an ionizable moiety. Polymerizable moieties can be those that permit free radical polymerization, including but not limited to acrylates, methacrylates, acrylamides, methacrylamides, vinyl groups, combinations thereof and derivatives thereof. Alternatively, other reactive chemistries can be employed to polymerize the polymer, such as but not limited to nucleophile/N-hydroxysuccinimide esters, nucleophile/halide, vinyl sulfone/acrylate or maleimide/acrylate. A polymerizable moiety can be an acrylate and/or an acrylamide.

Ionizing moieties can be added to impart the pH-sensitive solubility to the polymer. Ionizable moieties can include carboxylic acids, amines, and derivatives thereof. Alternatively or additionally, amines protected using any suitable technique, such as t-Boc, may be used in the synthesis of the liquid embolic polymer. Molecules containing polymerizable and ionizable moieties can include acrylic acid, methacrylic acid, aminopropyl methacrylamide, aminoethyl methacrylamide, N-(3-methylpyridine)acrylamide, N-(2-(4-aminophenyl)ethyl)acrylamide, N-(4-aminobenzyl)acrylamide, N-(2-(4-imidazolyl)ethyl)acrylamide, derivatives thereof and combinations thereof.

Other monomers can contain a polymerizable moiety and have a structure that facilitates the desired performance in dissolution or in precipitation. Polymerizable moieties can be those that permit free radical polymerization, including acrylates, methacrylates, acrylamides, methacrylamides, vinyl groups, and derivatives thereof. Alternatively or additionally, other reactive chemistries can be employed to polymerize the polymer, such as but not limited to nucleophile/N-hydroxysuccinimide esters, nucleophile/halide, vinyl sulfone/acrylate or maleimide/acrylate. In one embodiment, polymerizable moieties may be acrylates and acrylamides. In general, any monomer(s) can be utilized to form the described liquid embolic polymers.

Less hydrophobic monomers can require less ionizable monomer to be copolymerized with it to have the desired solubility characteristics. Likewise, more hydrophobic monomers can require more ionizable monomer to be copolymerized with it to have the desired solubility characteristics. Monomers containing moieties available for hydrogen bonding, such as hydroxyl groups, can increase the cohesiveness of the precipitated polymer. Monomers used can include acrylates and acrylamides such as alkyl acrylates, alkyl alkacrylates, alkyl alkacrylamides, and alkyl acrylamides. Acrylates and acrylamides can include but are not limited to t-butyl acrylate, t-butyl acrylamide, n-octyl methacrylate, methyl methacrylate, hydroxyethyl methacrylate, hydroxyethyl acrylate, hydroxypropyl methacrylate, hydroxybutyl methacrylate, derivatives thereof and combinations thereof.

In one embodiment, liquid embolic polymers can be polymerized from solutions, mixtures, prepolymer solutions of monomers with ionizable moieties and other monomers. The solvent used to dissolve the monomers can be any solvent that dissolves or substantially dissolves the chosen monomers. Solvents can include methanol, acetonitrile, dimethyl formamide, and dimethyl sulfoxide.

Polymerization initiators can be used to start the polymerization of the monomers in the solution. The polymerization can be initiated by reduction-oxidation, radiation, heat, or any other method known in the art. Radiation crosslinking of the monomer solution can be achieved with ultraviolet light or visible light with suitable initiators or ionizing radiation (e.g. electron beam or gamma ray) without initiators. Polymerization can be achieved by application of heat, either by conventionally heating the solution using a heat source such as a heating well, or by application of infrared light to the monomer solution.

In one embodiment, the polymerization initiator can azobisisobutyronitrile (AIBN) or a water soluble AIBN derivative (2,2'-azobis(2-methylpropionamidine) dihydrochloride). Other initiators can include N,N,N',N'-tetramethylethylenediamine, ammonium persulfate, benzoyl peroxides, azobisisobutyronitriles and combinations thereof. Initiator concentrations can range from about 0.25% w/w to about 2% w/w, about 0.5% w/w to about 1% w/w, about 0.25% w/w, about 0.5% w/w, about 0.75% w/w, about 1% w/w, about 1.25% w/w, about 1.50% w/w, about 1.75% w/w, about 2% w/w, of the mass of the monomers in solution or any range or value within the listed percentages. The polymerization reaction can be performed at elevated temperatures, of about 30° C. to about 200° C., about 50° C. to about 100° C., about 50° C., about 60° C., about 70° C., about 80° C., about 90° C. or about 100° C. After the polymerization is completed, the polymer can be recovered by precipitation in a non-solvent and dried under vacuum.

The aqueous solution with non-physiological pH can dissolve the liquid embolic polymer. In one embodiment, the aqueous solution does not include an organic solvent. Concentrations of the polymer in the aqueous solution can range from about 2.5% to about 25%, about 5% to about 15%, about 2.5%, about 5%, about 7.5%, about 10%, about 12.5%, about 15%, about 17.5%, about 20%, about 22.5%, about 25% or any percentage or range of percentages bound by the above percentages. The aqueous solution can contain the minimum amount of buffer to maintain the non-physiologic pH after dissolution of the liquid embolic polymer, but not adversely affect the pH of the patient after administration. Buffer concentrations range from about 1 mM to about 200 mM, about 10 mM to about 100 mM, about 20 mM to about 80 mM, about 30 mM to about 70 mM, about 40 mM to about 60 mM, about 45 mM to about 55 mM, about 10 mM, about 20 mM, about 30 mM, about 40 mM, about 50 mM, about 60 mM, about 70 mM, about 80 mM, about 90 mM, about 100 mM or any concentration or range of concentrations within the values listed. In other embodiments, the buffer concentration can be less than about 1 mM or even not used. In one embodiment, the buffer concentration can be about 25 mM.

For liquid embolic polymers containing amines, buffers can include citrate and acetate and solution pH's can be from about 3 to about 6, from about 3 to about 5, about 3, about 4, about 5 or about 6. For liquid embolic polymers containing carboxylic acids, buffers can include carbonate, N-cyclohexyl-2-am inoethanesulfonic acid (CHES), N-cyclohexyl-2-hydroxyl-3-aminopropanesulfonic acid (CAMPSO), N-cyclohexyl-3-aminopropanesulfonic acid (CAPS), 3-[4-(2-Hydroxyethyl)-1-piperazinyl]propanesulfonic acid (HEPPS or EPPS), 3-(N-morpholino)propanesulfonic acid (MOPS), 4-(2-hydroxyethyl)-1-piperazineethanesulfonic acid (HEPES), 2-(N-morpholino) ethanesulfonic acid (MES) and 2-amino-2-methyl-1-propanol (AMP) and solution pH's can be from about 8 to about 11, from about 8 to about 10, about 8, about 9, about 10 or about 11.

Particulate visualization and/or opacification agent or agents can impart visibility to the liquid embolic polymer when imaged using a medically relevant imaging technique such as fluoroscopy, computed tomography, or magnetic resonance techniques. Visualization of the polymer under fluoroscopy can be imparted by the incorporation of solid particles of radiopaque materials such as barium, bismuth, tantalum, platinum, gold, and other dense metals suspended in the non-physiological pH solution of the liquid embolic polymer. In one embodiment, the visualization agent for fluoroscopy can be barium sulfate. Visualization of the polymer under computed tomography imaging can be imparted by incorporation of solid particles of barium or bismuth. In one embodiment, the visualization agent for computed tomography imaging can be barium sulfate. Concentrations of barium sulfate to render the liquid embolic visible using fluoroscopic and computed tomography imaging can be from about 10% to about 30%, about 20% to about 30%, about 30% to about 50% w/w, about 40% to about 45% w/w, about 10%, about 13%, about 15%, about 17%, about 20%, about 23%, about 25%, about 27%, about 30%, about 33%, about 35%, about 37%, about 40%, about 43%, about 45%, about 47% about 50% of the non-physiological pH solution or any concentration or range of concentrations within the values listed.

In another embodiment, the visualization agent for fluoroscopy can be tantalum. Concentrations of tantalum to render the liquid embolic visible using fluoroscopic and/or computed tomography imaging can be from about 10% to about 30%, about 20% to about 30%, about 30% to about 50% w/w, about 40% to about 45% w/w, about 10%, about 13%, about 15%, about 17%, about 20%, about 23%, about 25%, about 27%, about 30%, about 33%, about 35%, about 37%, about 40%, about 43%, about 45%, about 47% about 50% of the non-physiological pH solution or any concentration or range of concentrations within the values listed.

Visualization of the liquid embolic polymer under magnetic resonance imaging can be imparted by the incorporation of solid particles of superparamagnetic iron oxide or gadolinium molecules polymerized into the polymer structure or encased into the polymeric structure once precipitated. One example visualization agent for magnetic resonance can be superparamagnetic iron oxide with a particle size of 10 microns. Concentrations of superparamagnetic iron oxide particles to render the hydrogel visible using magnetic resonance imaging range from about 0.01% w/w to about 1% w/w, about 0.05% w/w to about 0.5% w/w, or about 0.1% w/w to about 0.6% w/w of the polymerization solution.

Further, an iodinated compound can be used to impart visibility of the liquid embolic polymer when imaged using fluoroscopy or computer tomography. Dissolution of iohexol, iothalamate, diatrizoate, metrizoate, ioxaglate, iopamidol, ioxilan, iopromide, or iodixanol in the aqueous solution with non-physiological pH can render the radiopaque. Suspension of ethiodol, iodophenylundecylic acid, or both in the aqueous solution with non-physiological pH can render the liquid embolic polymer radiopaque.

In other embodiments, lipiodol ultra fluid which can include ethyl esters of iodized fatty acids of poppy seed oil qs ad for one ampoule with an iodine content of about 48% (i.e. 480 mg per mL). Additionally, in some embodiments, the use of iodinated compounds can provide temporary radiopacity of the polymer because the iodinated compounds can diffuse or otherwise be carried away from the embolization site by in vivo processes.

Polymer visualization under magnetic resonance imaging can be imparted by the incorporation of solid particles of superparamagnetic iron oxide or water soluble gadolinium compounds. In one embodiment, the visualization agent for magnetic resonance can be superparamagnetic iron oxide with a particle size of about 5 µm, about 10 µm or about 15 µm. Concentrations of superparamagnetic iron oxide particles with any of the above particle sizes to render the liquid embolic visible using magnetic resonance imaging can be from about 0.1% w/w to about 1% w/w, about 0.1% w/w, about 0.2% w/w, about 0.3% w/w, about 0.4% w/w, about 0.5% w/w, about 0.6% w/w, about 0.7% w/w, about 0.8% w/w, about 0.9% w/w, about 1% w/w of the non-physiological pH solution or any concentration or range of concentrations within the values listed.

If a particulate visualization agent is utilized, it can be prepared by dissolving the liquid embolic polymer in the aqueous solution with non-physiologic pH and adding the particulate agent. If a soluble visualization agent is utilized, it can be prepared by dissolving the liquid embolic polymer and water soluble visualization agent in an aqueous solution with non-physiologic pH.

The liquid embolic polymers, solutions and mixtures described herein can be sterilized without substantially degrading the polymer. After sterilization, at least about 50%, about 60%, about 70%, about 80%, about 90%, about 95% about 99% or about 100% of the polymer can remain intact. In one embodiment, the sterilization method can be autoclaving and can be utilized before administration of the polymer.

The liquid embolic polymer formulation can be removed from the vial using a needle and syringe, the syringe to be later connected to a delivery catheter. To prevent premature liquid embolic polymer deposition, the delivery catheter can be primed with a bolus of the same aqueous solution with non-physiologic pH as was used to dissolve the liquid embolic polymer. This flushing can prevent clogging of the delivery catheter with the liquid embolic polymer. The syringe containing the liquid embolic formulation can then be connected to the proximal end of a delivery catheter, such as a microcatheter, cannula, or the like, and positioned in the desired vascular or other anatomic site.

As the liquid embolic formulation is injected, it can push the aqueous solution with non-physiologic pH flushing solution out of the microcatheter. The rate of injection can provide differing precipitation amounts and/or precipitation performance. For example, a slower injection rate can achieve a more distal penetration of the liquid embolic polymer and a faster injection rate can achieve a more proximal penetration. In other embodiments, the opposite can be true. In yet another embodiment, a slower injection rate can result in more precipitation whereas a faster injection rate can result in less precipitation. In other embodiments, the opposite effect may occur. The speed of precipitation can be fast and in some cases can be immediate, e.g. faster than the human eye can discern. In other embodiments, the polymer can precipitate in less than about 60 s, about 50 s, about 40 s, about 30 s, about 20 s, about 10 s, about 5 s, about 4 s, about 3 s, about 2 s, about 1 s, about 0.75 s, about 0.5 s, about 0.25 s, about 0.1 s, about 0.05 s, about 0.01 s, about 0.001 s or any range encompassed by any of these values. For example, in one embodiment, the polymer can precipitate in between about 0.01 s and about 30 s.

The pH of the aqueous solution can then rapidly change to physiological pH as a result of the large buffering capacity of the body's tissues and fluids. Also, a low buffer strength of the solution can lead to the rapid change of pH. The progress of the liquid embolic formulation inside the delivery catheter can be observed using an imaging technique compatible with the particulate agent or agents selected. With continued injection, the liquid embolic formulation can enter a target delivery site or treatment site.

The large buffering capacity of the body's tissues can cause the fluids to rapidly deprotonate or protonate the ionizable moieties present on the liquid embolic polymer, thus reducing the solubility of the liquid embolic polymer and causing it to precipitate from solution. The precipitated liquid embolic polymer can entrap the particulate agents and can provide occlusion of the target site.

The precipitated liquid embolic polymer can be a solid mass of precipitate. In some embodiments, the mass can have less than about 20%, about 10%, about 5%, about 1%, about 0.1%, about 0.01, or about 0.001% fragmentation. In some embodiments, the precipitated polymer can be cohesive and remain substantially a solid mass.

The precipitated liquid embolic polymer can remain substantially stable once implanted. For example, the liquid embolic polymer can remain greater than about 60%, about 70% about 80%, about 90%, about 95%, about 99% or about 100% intact after about 5 days, about 2 weeks, about 1 month, about 2 months, about 6 months, about 9 months, about a year, about 2 years, about 5 years, about 10 years or about 20 years.

In some embodiments, however, it may be desirable for the precipitated liquid embolic polymer to degrade over time. In such embodiments, the liquid embolic polymer can degrade to less than about 40%, about 30% about 20%, about 10%, about 5% or about 1% intact after about 5 days, about 2 weeks, about 1 month, about 2 months, about 6 months, about 9 months, about a year, about 2 years, about 5 years, or about 10 years.

Further, the liquid embolic polymers once precipitated can be cohesive enough to stick to the tissue and/or remain in place through friction with the tissues. In other embodiments, the precipitated polymer can act as a plug in a vessel held in place by the flow and pressure of the blood itself.

Example 1

Polymer Preparation

To 3 mL of methanol, 1.6 g t-butyl acrylate, 0.4 g of aminoethyl methacrylate, and 10 mg of azobisisobutyronitrile were added. Upon complete dissolution, the solution was placed at 80° C. for 8 hr. Then, after cooling to room temperature, the polymer was recovered by precipitation in ethyl ether and dried under vacuum.

Example 2

Aqueous Solution Preparation

To 1 L of distilled water, 9 g sodium chloride and 6.81 g potassium phosphate monobasic were added. Upon complete dissolution, the pH of the solution was adjusted to 3 using phosphoric acid.

Example 3

Preparation of Liquid Embolic Polymer Formulation

To 9 g of the liquid of Example 2, 1 g of the polymer of Example 1 was added. Dissolution of the polymer was aided by incubating at 55° C. for 24 hr. After complete dissolution, 3 g of barium sulfate was added. The liquid embolic polymer formulation was then aliquoted into vials and capped. The vials were autoclaved at 121° C. for 15 min.

Example 4

Effect of Monomer Concentration on Solubility

Using the techniques described in Examples 1 and 2, the polymers described in Table 1 were prepared. The solubility of the polymers was investigated in aqueous solutions at pH 3 (non-physiological) and at pH 7.4 (physiological).

TABLE 1

| Polymer | Fraction t-butyl acrylate | Fraction aminopropyl methacrylate | Soluble at pH 3? | Soluble at pH 7.4? |
|---|---|---|---|---|
| 1 | 0.88 | 0.12 | No | No |
| 2 | 0.75 | 0.25 | Yes | No |
| 3 | 0.73 | 0.27 | Yes | No |
| 4 | 0.68 | 0.32 | Yes | Slightly |
| 5 | 0.65 | 0.35 | Yes | Slightly |
| 6 | 0.63 | 0.37 | Yes | Yes |

The results of Table 1 show how the solubility of the liquid embolic polymer can be controlled by the amount of ionizable moieties present in the polymer.

Example 5

In Vivo Evaluation of the Liquid Embolic Polymer in a Rabbit Kidney

Figure 2:
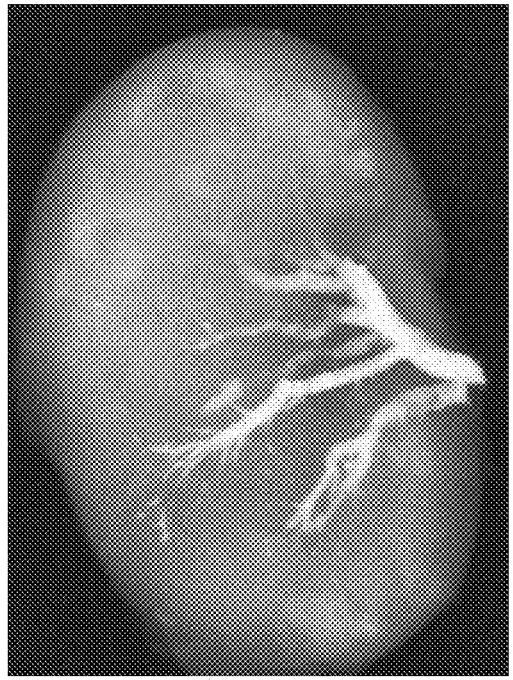
FIG. 2 illustrates an x-ray image of an excised kidney treated according to Example 5.
Figure 3:
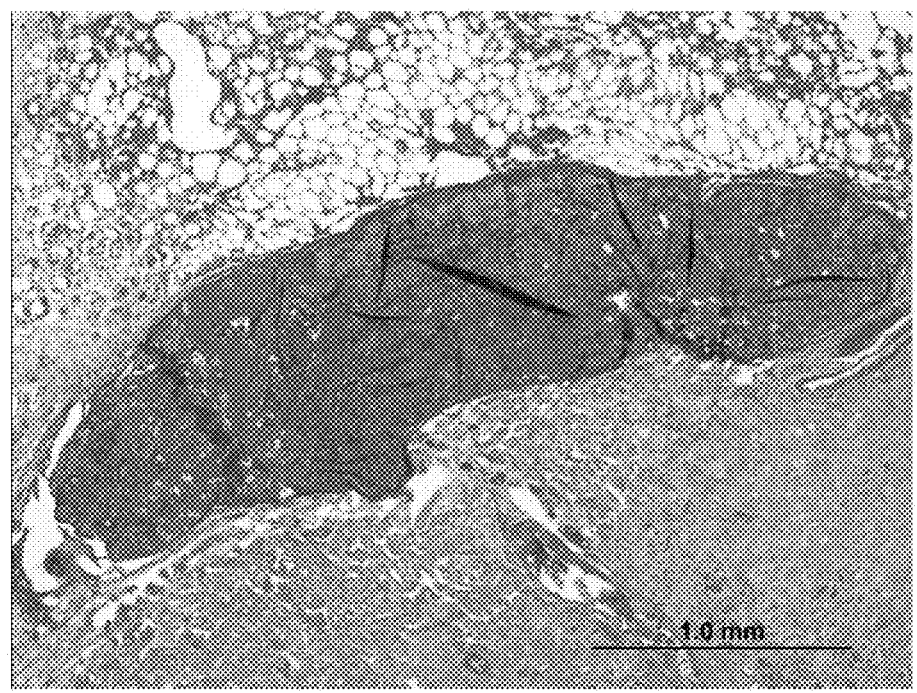
FIG. 3 illustrates a histological section of a renal artery filled with liquid embolic polymer.

The liquid embolic polymer formulation prepared according to the techniques of Examples 1, 2, and 3 was utilized for the embolization of five rabbit kidneys. Angiographic occlusion was obtained in all five kidneys. The kidneys remained occluded angiographically at the follow-up evaluation at 1 month (n=2, FIG. 1) and 3 months (n=3). Histological evaluation of the kidneys demonstrated good penetration of the liquid embolic polymer into the vasculature and substantial tissue destruction from the removal of the blood supply by the liquid embolic polymer (FIGS. 2 and 3).

Example 6

In Vivo Evaluation of the Liquid Embolic Polymer in a Porcine Rete

Figure 4A:
FIGS. 4A and 4B illustrate pre- and post-treatment angiograms of a rete in a pig according to Example 6.
Figure 4B:

The liquid embolic polymer formulation prepared according to the techniques of Examples 1, 2, and 3 was utilized for the embolization of a rete in an acute pig. At the end of the procedure, angiographic occlusion of the rete was obtained and can be seen when comparing the pre-treatment angiogram in FIG. 4A and the post-treatment angiogram in FIG. 4B.

Example 7

CT Evaluation of the Liquid Embolic Polymer

The liquid embolic polymer formulation prepared according to the techniques of Examples 1, 2, and 3 was utilized for the embolization of the renal vasculature of rabbits. The liquid embolic formulation was opacified with barium sulfate. At the end of the procedure, the rabbit was imaged using a CT scanner and differences can be seen when comparing the pre-treatment angiogram in FIG. 5A and the post-treatment CT angiogram in FIG. 5B.

Example 8

MR Evaluation of the Liquid Embolic Polymer

Figure 6:
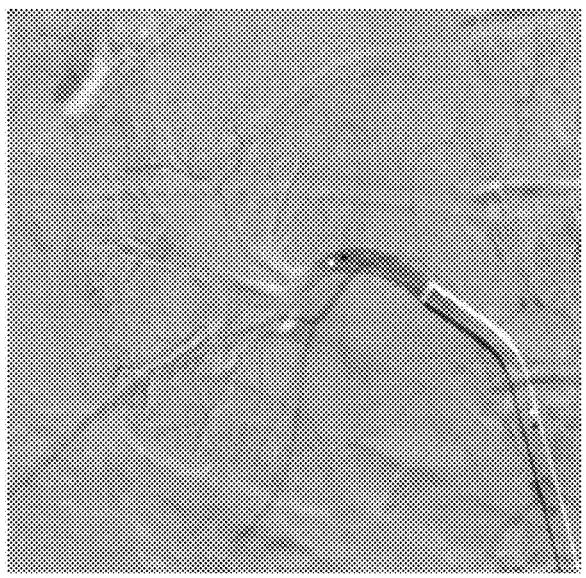
FIG. 6 illustrates a post treatment angiogram using barium sulfate of renal vasculature in a rabbit according to Example 8.
Figure 7A:
FIGS. 7A and 7B illustrate a post treatment angiogram and a post-treatment MR angiogram using tantalum of a renal vasculature in a rabbit according to Example 8 for visualization comparison.
Figure 7B:
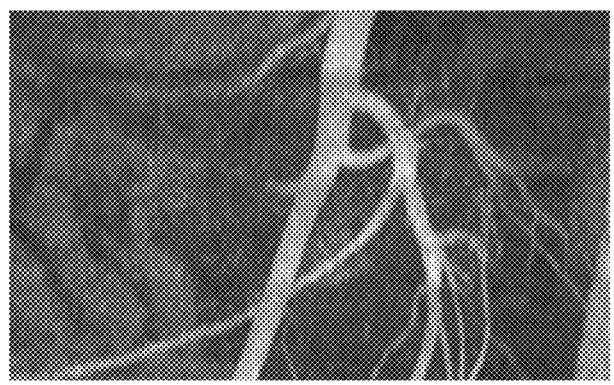

The liquid embolic polymer formulation prepared according to the techniques of Examples 1, 2, and 3 was utilized for the embolization of the renal vasculature of rabbits. The liquid embolic formulation was opacified with either tantalum or barium sulfate. At the end of the procedure, the rabbits were imaged using a MR scanner and differences can be seen when comparing the pre-treatment angiogram in FIGS. 6 and 7A and the post-treatment MR angiogram in FIG. 7B.

Example 9

Preparation of Polymer with Increased Cohesivity

To 3 mL of methanol, 0.5 g t-butyl acrylate, 1.2 g hydroethyl methacrylate, 0.3 g of aminoethyl methacrylate, and 10 mg of azobisisobutyronitrile were added. Upon dissolution of all components, the solution was placed at 80° C. for 8 hr. After cooling to room temperature, the polymer was recovered by precipitation in ethyl ether and dried under vacuum.

Example 10

Preparation of Aqueous Solution with Non-physiological pH and Soluble Iodine To 1 L of distilled water, 9 g sodium chloride, 6.81 g potassium phosphate monobasic, and 200 g iohexol were added. Upon dissolution of all components, the pH of the solution was adjusted to 3 using phosphoric acid.

Example 11

Preparation of Liquid Embolic Polymer Formulation

To 9 g of the liquid of Example 11, 1 g of the polymer of Example 10 was added. Dissolution of the polymer was aided by incubating at 55° C. for several hours. After dissolution of the liquid embolic polymer, the liquid embolic polymer formulation was then aliquoted into vials and capped. The vials were autoclaved at 121° C. for 15 min.

Example 12

Comparison of Liquid Embolic Polymer Formulation Precipitation

The liquid embolic polymer formulations of Examples 3 and 11 were evaluated by adding each formulation drop wise into excess phosphate buffered saline at pH 7.4. The speed of precipitation and cohesiveness of the precipitate were evaluated. Results are included in Table 2.

TABLE 2

|  | Speed of Precipitation | Cohesiveness of Precipitate |
| --- | --- | --- |
| Example 3 Formulation | Immediate | Multitude of polymer pieces |
| Example 11 Formulation | Immediate | Single piece of polymer |

Example 13

Liquid Embolic for Use in a Basic pH Environment

To 3 mL of methanol, 1.6 g t-butyl acrylate, 0.4 g of aminoethyl methacrylate, and 10 mg of azobisisobutyronitrile were added. Upon dissolution of components, the solution was placed at 80° C. for 8 hr. After cooling to room temperature, the polymer was recovered by precipitation in ethyl ether and dried under vacuum. To 1 L of distilled water, 9 g sodium chloride and 6.81 g potassium phosphate monobasic were added. Upon dissolution of components, the pH of the solution was adjusted to 3 using phosphoric acid.

To 9 g of the liquid, one gram of the polymer was added. Dissolution of the polymer was aided by incubating at 55° C. for 24 hr. After dissolution of the liquid embolic polymer, 7 g of barium sulfate was added to the solution. The liquid embolic formulation was then aliquoted into vials and capped. The vials were autoclaved at 121° C. for 30 min.

Such a liquid embolic formulation can be implanted as described herein into intestines or other high pH environments where the polymer precipitates.

Example 14

Liquid Embolic for Use in an Acidic pH Environment

To 3 mL of methanol, 0.5 g n-octyl methacrylate, 1.5 g of methacrylic acid, and 10 mg of azobisisobutyronitrile were added. Upon dissolution of components, the solution was placed at 80° C. for 8 hr. After cooling to room temperature, the polymer was recovered by precipitation in ethyl ether and dried under vacuum. To 1 L of distilled water, 9 g sodium chloride and 4.2 g sodium bicarbonate were added. Upon dissolution of components, the pH of the solution was adjusted to 10 using sodium hydroxide.

To 9 g of the liquid, one gram of the polymer was added. Dissolution of the polymer was aided by incubating at 55° C. for 24 hr. After dissolution of the liquid embolic polymer, 7 g of barium sulfate was added to the solution. The liquid embolic formulation was then aliquoted into vials and capped. The vials were autoclaved at 121° C. for 30 min.

Such a liquid embolic formulation can be implanted as described herein into a stomach or other low pH environments where the polymer precipitates.

Unless otherwise indicated, all numbers expressing quantities of ingredients, properties such as molecular weight, reaction conditions, and so forth used in the specification and claims are to be understood as being modified in all instances by the term "about." Accordingly, unless indicated to the contrary, the numerical parameters set forth in the specification and attached claims are approximations that may vary depending upon the desired properties sought to be obtained by the present invention. At the very least, and not as an attempt to limit the application of the doctrine of equivalents to the scope of the claims, each numerical parameter should at least be construed in light of the number of reported significant digits and by applying ordinary rounding techniques. Notwithstanding that the numerical ranges and parameters setting forth the broad scope of the invention are approximations, the numerical values set forth in the specific examples are reported as precisely as possible. Any numerical value, however, inherently contains certain errors necessarily resulting from the standard deviation found in their respective testing measurements.

The terms "a," "an," "the" and similar referents used in the context of describing the invention (especially in the context of the following claims) are to be construed to cover both the singular and the plural, unless otherwise indicated herein or clearly contradicted by context. Recitation of ranges of values herein is merely intended to serve as a shorthand method of referring individually to each separate value falling within the range. Unless otherwise indicated herein, each individual value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein is intended merely to better illuminate the invention and does not pose a limitation on the scope of the invention otherwise claimed. No language in the specification should be construed as indicating any non-claimed element essential to the practice of the invention.

Groupings of alternative elements or embodiments of the invention disclosed herein are not to be construed as limitations. Each group member may be referred to and claimed individually or in any combination with other members of the group or other elements found herein. It is anticipated that one or more members of a group may be included in, or deleted from, a group for reasons of convenience and/or patentability. When any such inclusion or deletion occurs, the specification is deemed to contain the group as modified thus fulfilling the written description of all Markush groups used in the appended claims.

Certain embodiments of this invention are described herein, including the best mode known to the inventors for carrying out the invention. Of course, variations on these described embodiments will become apparent to those of ordinary skill in the art upon reading the foregoing description. The inventor expects skilled artisans to employ such variations as appropriate, and the inventors intend for the invention to be practiced otherwise than specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

In closing, it is to be understood that the embodiments of the invention disclosed herein are illustrative of the principles of the present invention. Other modifications that may be employed are within the scope of the invention. Thus, by way of example, but not of limitation, alternative configurations of the present invention may be utilized in accordance with the teachings herein. Accordingly, the present invention is not limited to that precisely as shown and described.

We claim:

1. A composition comprising:
   a biocompatible polymer comprising:
   a first monomer wherein the first monomer is t-butyl acrylate;
   a second monomer wherein the second monomer is an alkyl acrylate comprising a hydroxyl group; and
   a third monomer wherein the third monomer is hydroxyethyl methacrylate;
   a pH-sensitive component, wherein the pH-sensitive component is selected from aminopropyl methacrylamide, aminoethyl methacrylamide, N-(3-methylpyridine)acrylamide, N-(2-(4-aminophenyl)ethyl)acrylamide, N-(4-aminobenzyl)acrylamide, N-(2-(4-imidazolyl)ethyl)acrylamide, derivatives thereof, and combinations thereof;
   an aqueous solution with a non-physiological pH; and
   a visualization agent;
   wherein the biocompatible polymer is soluble in the aqueous solution and insoluble at a physiological pH at a treatment site.

2. The composition of claim 1, wherein the visualization agent is a particulate.

3. The composition of claim 1, wherein the visualization agent has a concentration of about 5% w/w to about 65% w/w.

4. The composition of claim 1, wherein the visualization agent is barium sulfate or tantalum.

5. The composition of claim 1, wherein the non-physiological pH solution is water.

6. The composition of claim 1, wherein the non-physiological pH solution has a pH of less than about 6.

7. The composition of claim 1, wherein the biocompatible polymer has a concentration of about 1% w/w to about 35% w/w.

8. The composition of claim 1, wherein the biocompatible polymer further includes a polymerization initiator.

9. The composition of claim 8, wherein the polymerization initiator is azobisisobutyronitrile.

10. The composition of claim 8, wherein the polymerization initiator has a concentration of about 0.25% w/w to about 2% w/w.

11. The composition of claim 1, wherein the pH-sensitive component is aminopropyl methacrylamide.

* * * * *